Jan. 21, 1941. E. C. BOSLEY Plant Pat. 441
HYBRID TEA ROSE PLANT
Filed Aug. 21, 1940
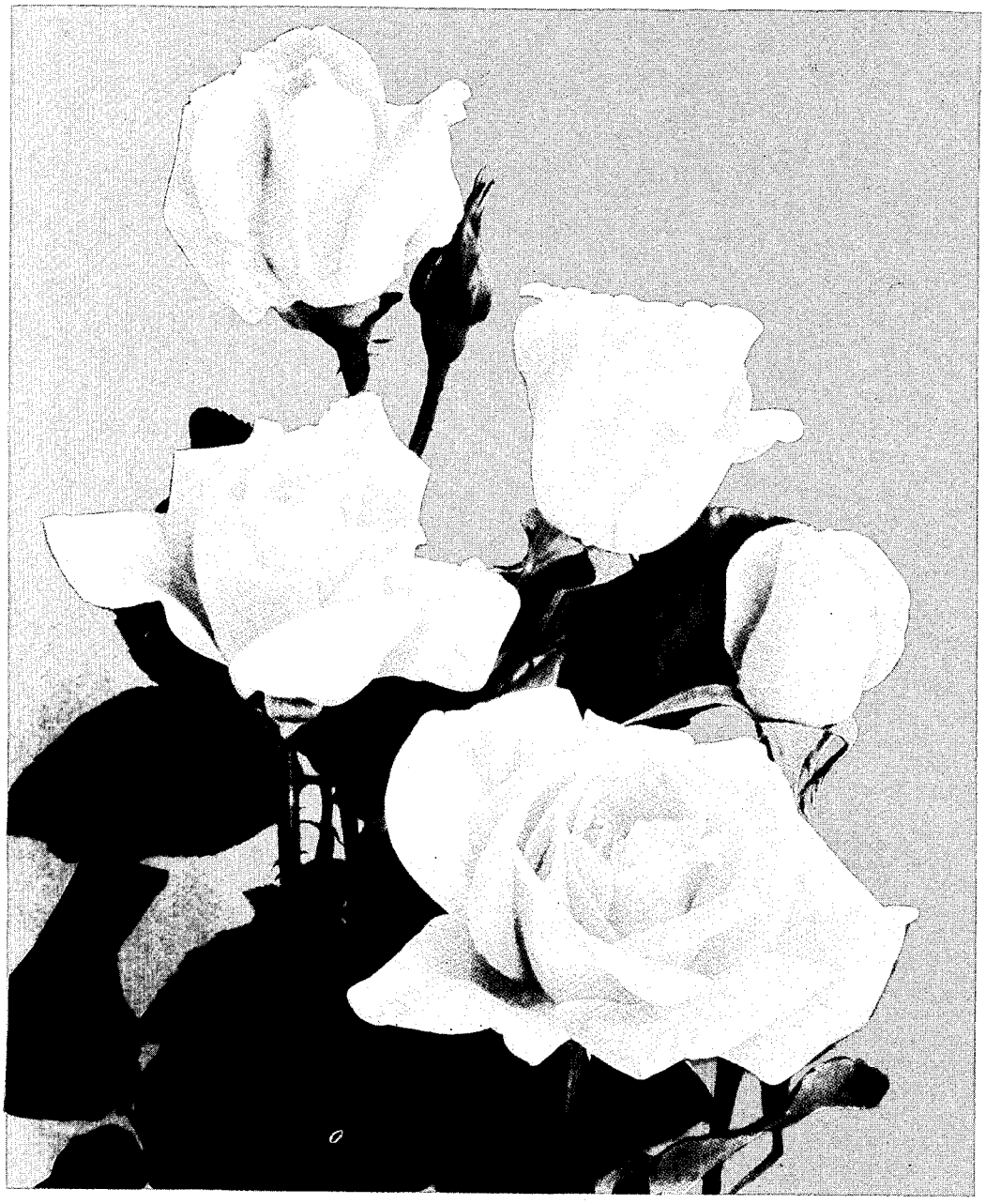
INVENTOR
Edith C. Bosley
By Orville M. Kile
Plant Patent Agt Patented Jan. 21, 1941

UNITED STATES PATENT OFFICE

441

HYBRID TEA ROSE PLANT

Edith C. Bosley, Mentor, Ohio

Application August 21, 1940, Serial No. 353,583

1 Claim. (Cl. 47—61)

My present discovery originated as a sport branch of a Mme. Joseph Perraud rose plant and was discovered by me growing in the gardens of the Bosley Nursery. The variety has been asexually reproduced for several years and during that time I have been improving the richness of its color by careful bud selection. Observations relating to description of this new variety are made under average outdoor conditions prevailing in Mentor, Ohio, and with the plants growing in clay loam soil.

The principal novel feature of my new rose variety is the distinct yellow to orange color of its flowers and its extra long bud, but it is characterized also by the very high quality of its flowers and the fact that each bud develops into a flower of cutting value, with good stiff stems. In other respects my new variety is approximately like its parent.

The original illustrations accompanying this application show five opening flowers and two tight buds of this new variety, together with some of its stems and foliage. These are shown in approximately their true colors when observed in favorable summer conditions. Other observations in early spring and in the very hot summer showed the flowers to have less depth of color.

Following is a description of the plant and flower of this new variety of rose. Colors are indicated by reference to Ridgway's Color Standards and Nomenclature except where obviously the ordinary dictionary term is intended.

*The plant*

Growth: Compact bush, having tendency to throw long stems from the base. Usually grows 2 to 3 feet in height.

Blooming habit: Tends to bloom in monthly bursts throughout the season. Usually borne singly on long stems but sometimes blooms in groups of 3 or more, depending on seasonal conditions.

Disease resistance: Fairly resistant to blackspot and mildew.

New wood: Light green, becoming dark green.

Foliage:

*Quantity.*—Ample but not abundant.

*Leaflets.*—Usually 5, often 3 and occasionally 7.

*Size.*—Medium to large. Terminal leaflet averages 2⅝ by 1¾ inches. First set of lateral leaflets are approximately the same size as the terminal but other laterals are smaller.

*Shape.*—Oval, with acute to acuminate apex and rounded base.

*Margin.*—Sharply serrated; sometimes serrations are compound.

*Rachis.*—Grooved above; carries several large sized, sharp prickles of whitish green color, on under side.

*Color.*—Mature foliage is Elm Green (Plate XVII) on upper surface, sometimes with midrib of approximately Vinaceous Rufous (Plate IV). The under surface is approximately Light Elm Green (Plate XVII). The younger foliage is Biscay to Courge Green (Plate XVII), frequently edged with Ocher Red (Plate XXVII).

*Stipules.*—Long; narrow; clinging; with exceptionally long points.

Stems: Strong; Oil Green (Plate V); usually 8 to 10 inches long.

Thorns:

*Quantity.*—Average number on main stems. Large number on lateral stems.

*Size.*—Medium.

*Position.*—Irregular and close together; often found in groups of three encircling the stem.

*Prickles.*—A large number of prickles are also present and irregularly placed on stem.

*Color.*—Vinaceous Rufous (Plate XIV), changing to whitish green.

*The flower*

Bud:

*Size.*—Extra long, sometimes 2 to 2¼ inches in length.

*Form.*—Slender, pointed, often becoming urn-shaped.

*Peduncle.*—Medium in length; covered with many prickles.

*Calyx.*—Fairly simple; points extend beyond closed bud. Sepals usually have one or two slight lateral branches on each edge. Outside is Cress Green (Plate XXXI), inside is Deep Grape Green (Plate XLI) with a covering of white fuzz. Calyx of young buds is tipped with Ochre Red (Plate XXVII).

*Color.*—When first open the bud is Apricot Yellow (Plate IV) blending to Lemon Chrome (Plate IV) at base, and splashed with tones of Scarlet (Plate I) and Peach Red (Plate I) where calyx first divides. Opening bud is Deep Chrome (Plate III) blending through Capucine Yellow (Plate III), with slight touches of Orange Chrome (Plate II) and Flame Scarlet (Plate II) in center depths. Outside of petals is Light Cadmium (Plate IV), at extreme base, blending through Cadmium Yellow (Plate III) to Capucine Yellow (Plate III).

Blossom:

*Size.*—Medium, averages 3½ to 4 inches across.

*Form.*—High centered, retaining shape. Petals roll back slightly.

*Petalage.*—Averages 40 petals, with addition of several petaloids.

*Color.*—Under the most favorable conditions the face of petals is Apricot Yellow (Plate IV) and Light Orange Yellow (Plate III), with touches of Deep Chrome (Plate III) and Capucine Orange (Plate III) in extreme depths. Outer surface of petals is Orange-Buff (Plate III) and Light Orange-Yellow (Plate III) blending to Light Cadmium (Plate IV) at the base. In some cases the mature flower is uniformly yellow, approximately Apricot Yellow (Plate IV).

Petals:

*Texture.*—Heavy.

*Shape.*—Outer petals nearly round with slight, irregular notches at tip. Petals begin in early stages of opening to roll back gently, thus changing their apparent shape.

*Fragrance.*—Moderate.

*Aspect.*—Silky.

*Lasting quality.*—Excellent as cut flowers.

*Persistence.*—Clinging.

Reproductive organs:

*Pistils.*—Very numerous; loosely bunched. *Styles* yellow, with red tinge just below tip. *Stigmas* light yellow.

*Stamens.*—Many; surround bunched pistils. *Filaments* light yellow, uneven lengths. *Anthers* darker yellow edged with light brown.

Having thus disclosed my discovery, I claim:

The new and distinct variety of hybrid tea rose plant herein shown and described, of the general type of the Mme. Joseph Perraud variety but characterized particularly by its extra long bud, also by the high percentage of perfect development of its buds into flowers of cutting value; and the high quality and yellow to orange color of its flowers substantially as described.

EDITH C. BOSLEY.